United States Patent [19]

Ross et al.

[11] 4,215,134
[45] Jul. 29, 1980

[54] 4-HYDROXY-2-BENZIMIDAZOLINE-THIONE COMPOUNDS AND PHARMACEUTICAL COMPOSITIONS CONTAINING THEM

[75] Inventors: Carl H. Ross, Viernheim; Walter-Gunar Friebe, Darmstadt; Wolfgang Kampe, Heddesheim; Wolfgang Bartsch, Viernheim; Egon Roesch, Mannheim, all of Fed. Rep. of Germany

[73] Assignee: Boehringer Mannheim GmbH, Mannheim, Fed. Rep. of Germany

[21] Appl. No.: 2,129

[22] Filed: Jan. 9, 1979

[30] Foreign Application Priority Data

Jan. 18, 1978 [DE] Fed. Rep. of Germany ....... 2801980

[51] Int. Cl.² .................. A61K 31/415; C07D 235/28
[52] U.S. Cl. ................................. 424/273 B; 548/305
[58] Field of Search ..................... 548/305; 424/273 B

[56] References Cited

U.S. PATENT DOCUMENTS

| 4,073,929 | 2/1978 | Callery | 548/305 |
| 4,085,221 | 4/1978 | Smith | 548/305 |
| 4,140,789 | 2/1979 | Jaeggi et al. | 548/305 |

FOREIGN PATENT DOCUMENTS 2819458 11/1978 Fed. Rep. of Germany .

OTHER PUBLICATIONS

Conant et al., The Chemistry of Organic Compounds 3rd Ed., p. 342, N.Y., Macmillan, 1947.
Fauland et al., Chem. Abst. 1976, vol. 84, No. 135665a.

*Primary Examiner*—Natalie Trousof
*Attorney, Agent, or Firm*—Sprung, Felfe, Horn, Lynch & Kramer

[57] ABSTRACT

Novel 4-hydroxy-2-benzimidazoline-thione compound of the formula:

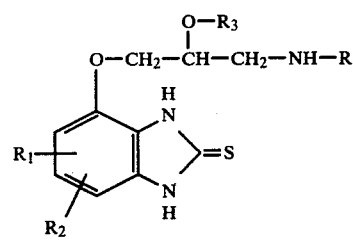

wherein
R is lower alkyl;
$R_1$ and $R_2$, which can be the same or different, are hydrogen or lower straight-chained or branched alkyl or
$R_1$ and $R_2$ together represent alkylene; and
$R_3$ is a hydrogen atom or an acyl radical;

and the pharmacologically acceptable salts thereof; have marked β-receptor blocking action and are outstandingly useful in the treatment or prophylaxis of cardiac and circulatory diseases.

20 Claims, No Drawings

4-HYDROXY-2-BENZIMIDAZOLINE-THIONE COMPOUNDS AND PHARMACEUTICAL COMPOSITIONS CONTAINING THEM

The present invention relates to new 4-hydroxy-2-benzimidazoline-thione compounds, to pharmaceutical compositions containing them, and to methods for treating cardiac and circulatory deficiencies utilizing such compounds.

German Patent Specification No. 2,700,193 describes 4-hydroxy-2-benzimidazolinone derivatives with a β-receptor-blocking activity. It has now been found that 4-hydroxy-2-benzimidazoline-thione derivatives also possess an outstanding β-receptor-blocking action and, therefore, can also be used for the treatment or prophylaxis of cardiac and circulatory diseases.

Thus, according to the present invention, there are provided basically-substituted derivatives of 4-hydroxy-2-benzimidazoline-thione of the general formula:

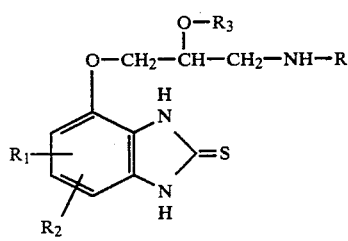 (I)

wherein
R is lower alkyl,
$R_1$ and $R_2$, which can be the same or different, are hydrogen or lower, straight-chained or branched alkyl, or
$R_1$ and $R_2$ together represent an alkylene radical, and
$R_3$ is hydrogen or an acyl (e.g., alkanoyl); and the pharmacologically acceptable salts thereof.

The compounds of general formula (I) contain an optically-active carbon atom in the aminopropoxy side chain and can, therefore, occur not only in racemic form but also in two optically-active forms. The present invention includes not only the racemic forms but also the optical isomers.

The lower alkyl radicals in the definitions of the substituents R, $R_1$ and $R_2$ can contain up to 6 and preferably up to 4 carbon atoms, the methyl, isopropyl and tert.-butyl radicals being preferred.

The alkylene radicals which can be formed by the substituents $R_1$ and $R_2$ contain 2 to 4 carbon atoms.

The acyl radicals $R_3$ can be acid residues of straight-chained or branched aliphatic carboxylic acids containing 2 to 6 carbon atoms or of aromatic carboxylic acids optionally substituted by halogen atoms, lower alkyl radicals or lower alkoxy radicals, the preferred acyl radicals being the acetyl, pivaloyl and benzoyl radicals.

The new compounds (I), as well as their pharmacologically acceptable salts, bring about an inhibition of adrenergic β-receptors and can, therefore, be used for the treatment and prophylaxis of cardiac and circulatory diseases.

The new compounds (I) according to the present invention can be prepared, for example, by one of the following methods:

(a) reaction of a compound of the general formula:

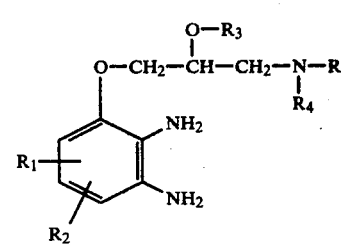 (II)

with a compound of the general formula:

W-R   (III)

in which R, $R_1$ and $R_2$ have the same meanings as above, whereas U stands for a $>C=O$ or $>CH-OZ$ group, Z having the same meaning as $R_3$ or also, together with V, representing a single bond, and one of the symbols V and W represent an amino group and the other a reactive residue and, when U is a $>C=O$ group, subsequent reduction of the product obtained; or (b) reaction of a compound of the general formula:

$$O-CH_2-\underset{\underset{O-R_3}{|}}{CH}-CH_2-\underset{\underset{R_4}{|}}{N}-R$$ (IV)

(with structure showing $R_1$, $R_2$, $NH_2$, $NH_2$ substituents on benzene ring)

in which R, $R_1$, $R_2$ and $R_3$ have the same meanings as above and $R_4$ is a hydrogen atom or a protective group which can be split off, with a compound of the general formula:

$Y_1-CS-Y_2$   (V)

in which $Y_1$ and $Y_2$, which can be the same or different, are reactive residues, whereafter, when a protective group $R_4$ is present, this is again split off; or (c) reaction of a compound of the general formula:

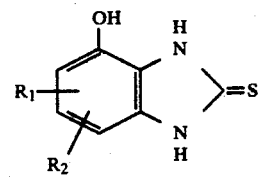 (VI)

in which $R_1$ and $R_2$ have the same meanings as above, with a compound of the general formula:

$L-CH_2-M-CH_2-\underset{\underset{R_4}{|}}{N}-R$   (VII)

in which R and $R_4$ have the same meanings as above, M stands for a $>C=O$ or $>CH-OZ$ group, whereby Z has the same meaning as $R_3$ or, together with L can also represent a single bond, and L is a reactive residue, whereafter, when M is a $>C=O$ group, the product obtained is subsequently reduced and a protective group $R_4$ possibly present is again split off; and, subsequent to the reaction, compounds obtained of general formula (I) are, if desired, converted into pharmacologically acceptable salts, whereby, in the case of compounds of general formula (I) in which R₃ is a hydrogen atom, the hydroxyl group is, if desired, previously acylated.

Y₁ and Y₂ in compounds of general formula (V) can be any residues which are able to react with the two primary amino groups in compounds of general formula (IV) to give an imidazoline ring. Such residues are preferably halogen atoms, such as bromine or chlorine atoms, or amino, imidazolyl, lower alkoxy, lower acyloxy, mercapto or lower alkoxythiocarbonyl radicals. Thus, for example, as compounds of general formula (V), there can be used thiocarbonyl halides, thiourea or also xanthogenates. Compounds of general formula (V) can also be prepared in situ in the reaction mixture from other compounds, for example carbon disulphide in alkaline solution.

The processes according to the present invention are preferably carried out in a solvent which is inert under the reaction conditions, for example, water, ethanol, dioxan or dimethylformamide, possibly in the presence of an acid-binding agent. The reactions can also be achieved after mixing the reaction components, without the use of a solvent. The reactions are carried out by leaving the reaction mixture to stand at ambient temperature or by heating, possibly under a protective gas atomsphere.

When the reduction of a $>C=O$ group is to be carried out, this can take place by catalytic hydrogenation with a noble metal or nickel catalyst or by means of a complex hydride, for example sodium borohydride.

As protective groups which can easily be split off, there can, in principle, be used all protective groups used in peptide chemistry for the intermediate protection of amino groups which, after the reaction has taken place, can be removed again. In the case of the reactions according to processes (b) and (c), it is especially advantageous to use a benzyl or carbobenzoxy radical which, after the reaction of a compound of general formula (IV) and (VI) with a compound of general formula (V) or (VII), respectively, can readily be split off hydrogenolytically in known manner.

The compounds of general formula (IV) can be prepared, for example, by reacting a compound of the general formula:

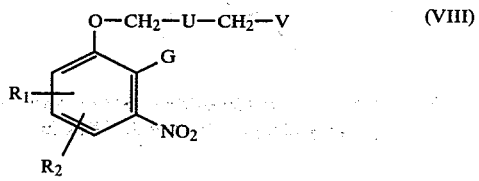

(VIII)

in which R₁, R₂, U and V have the same meanings as above, and G is an amino or nitro group, with a compound of general formula (III) analogously to process (a) and then reducing the product thus obtained, the reduction being carried out in known manner, preferably by catalytic hydrogenation. The crude o-phenylenediamine derivatives of general formula (IV) thus obtained are advantageously employed, without purification, as mineral acid salts as starting materials in process (b).

The compounds of general formula (VIII) are either known compounds or can easily be prepared from known compounds by known methods.

The subsequent acylation of compounds of general formula (I), in which R₃ is a hydrogen atom, which is possibly to be carried out can take place in the usual manner by reaction with a reactive acid derivative, for example, an acid halide, acid azide or acid anhydride, possibly in the presence of an acid-binding agent, for example pyridine, in a solvent, for example, acetone, benzene, dimethylformamide or also in excess acid.

The compounds of general formula (I) according to the present invention can be obtained in the form of a racemic mixture. The separation of the racemate into the optically-active forms takes place by known methods via the diastereomeric salts with optically-active acids, for example, tartaric acid, malic acid or camphorsulphonic acid.

The new compounds of general formula (I) are usually obtained, under the reaction conditions of the above-described processes, as acid-addition salts, for example as hydrochlorides, and can readily be converted into the corresponding free bases in known manner.

For the conversion of compounds of general formula (I) into their pharmacologically acceptable salts, the compounds are reacted, preferably in an organic solvent, with an equivalent amount of an inorganic or organic acid, for example, hydrochloric acid, hydrobromic acid, phosphoric acid, sulphuric acid, acetic acid, citric acid or maleic acid.

For the production of pharmaceutical compositions, the compounds (I) are mixed in the usual manner with appropriate pharmaceutical carrier substances and/or aroma, flavouring and colouring materials and formed, for example, into tablets or dragees or, with the addition of appropriate adjuvants, suspended or dissolved in water or in an oil, for example olive oil.

The new compounds (I) according to the present invention and the salts thereof can be administered enterally or parenterally in liquid or solid form. As injection medium, it is preferable to use water which contains the conventional additives for injection solutions, for example stabilising agents, solubilising agents and/or buffers. Additives or this type include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and/or sweetening agents.

Preferred compounds according to the present invention are, apart from those mentioned in the Examples, also the following compounds:
4-(2-benzoyloxy-3-tert.-butylaminopropoxy)-6-methyl-2-benzimidazoline-thione,
4-(2-hydroxy-3-tert.-butylaminopropoxy)-6,7-cyclopentenobenzimidazoline-thione, and
7-tert.-butyl-4-(2-hydroxy-3-tert.-butylaminopropoxy)-2-benzimidazoline-thione.

The following Examples are given for the purpose of illustrating the present invention. They describe some of the numerous possible process variants which can be used for the synthesis of the compounds according to the present invention.

EXAMPLE 1

4-(2-Hydroxy-3-tert.-butylaminopropoxy)-2-benzimidazoline-thione.

7.2 g. 2,3-Diamino-1-(2-hydroxy-3-tert.-butylaminoproxy)-benzene (see German Patent Specification No. 2,432,269) are dissolved in 20 ml. ethanol and mixed with 1.26 g. potassium hydroxide, 1.73 g. carbon disulphide and 2.9 ml. water. The reaction mixture is boiled under reflux for 3 hours. After clarification with active charcoal, the solution is mixed at 70° C. with 1.6 ml. glacial acetic acid in 23 ml. water and then evaporated to dryness. After crystallisation of the evaporation residue from ethanol, there are obtained 2.4 g. (40% of theory) of free base with a melting point of 214°–216° C. which is converted in ethanolic solution with ethereal hydrochloric acid into the corresponding 4-(2-hydroxy-3-tert-butylaminopropoxy)-2-benzimidazoline-thione hydrochloride; m.p. 288°–289° C.

EXAMPLE 2

4-[2-Hydroxy-3-(2-propylamino)-propoxy]-2-benzimidazoline-thione

From 2,3-diamino-1-[2-hydroxy-3-(2-propylamino)-propoxy]-benzene, using the process described in Example 1, there is obtained the title compound in the form of its hydrochloride; m.p. 254° C.

EXAMPLE 3

4-Hydroxy-3-tert.-butylaminopropoxy)-6-methyl-2-benzimidazoline-thione 14.3 g. 2,3-Diamino-1-(2-hydroxy-3-tert.-butylaminopropoxy)-5-methylbenzene (obtainable from the trihydrochloride by mixing with the stoichiometric amount of sodium methylate solution and evaporation), 9.4 g. potassium xanthogenate, 55 ml. ethanol and 8 ml. water are boiled under reflux for 10 hours. After mixing with 12 ml. concentrated hydrochloric acid, the reaction mixture is again briefly boiled and then evaporated to dryness. After recrystallisation from 500 ml. water and 100 ml. dimethylformamide, with the addition of active charcoal, there are obtained 10.2 g. (55% of theory) colourless crystals of 4-(2-hydroxy-3-tert.-butylaminopropoxy)-6-methyl-2-benzimidazoline-thione hydrochloride; m.p. 295°–296° C. (decomp.).

The diamino compound required as intermediate can be prepared in the following manner:

By nitration of previously acetylated 2-amino-5-methylphenol (m.p. 156°–158° C.) at 30° C. in glacial acetic acid with nitric acid in acetic anhydride, there is obtained 1-acetoxy-2-acetamido-3-nitro-5-methylbenzene; m.p. 163°–165° C. Saponification thereof with 2 N hydrochloric acid gives 2-amino-5-methyl-3-nitrophenol; m.p. 197°–199° C. From this compound, by reaction with 3-chloro-1,2-epoxy-propane and 25% aqueous sodium hydroxide solution at 75° C., there is obtained 2-(2,3-epoxypropoxy)-4-methyl-6-nitroaniline; m.p. 90°–91° C. Reaction of this compound with tert.-butylamine in ethanol and subsequent catalytic hydrogenation over platinum dioxide gives, after acidification with hydrochloric acid, amorphous 2,3-diamino-1-(2-hydroxy-3-tert.-butylaminopropoxy)-5-methylbenzene trihydrochloride.

EXAMPLE 4

4-[2-Hydroxy-3-(2-propylamino)-propoxy]-6-methyl-2-benzimidazoline-thione

From potassium xanthogenate and 2,3-diamino-1-[2-hydroxy-3-(2-propylamino)-propoxy]-5-methylbenzene, using the process described in Example 3, there is obtained the title compound which, after recrystallisation from ethanol, decomposes at 294°–295° C.

The diamine used as intermediate is obtained by reaction of the 2-(2,3-epoxypropoxy)-4-methyl-6-nitroaniline described in Example 3 with 2-propylamine to give 2-[2-hydroxy-3-(2-propylamino)-propoxy]-4-methyl-6-nitroaniline, followed by catalytic hydrogenation.

EXAMPLE 5

4-(2-Pivaloyloxy-3-tert.-butylaminopropoxy)-6-methyl-2-benzimidazoline-thione 3.45 g. 4-(2-hydroxy-3-tert.-butylaminopropoxy)-6-methyl-2-benzimidazoline-thione hydrochloride (see Example 3) are converted with the stoichiometric amount of methanolic sodium methylate solution into the free base. This is reacted with 12 g. pivalic acid anhydride in 80 ml. dimethylformamide for 4 days at ambient temperature. The crystalline deposit is treated with ethereal hydrochloric acid and, after evaporation, recrystallised from ethanol. There is obtained 4-(2-pivaloyloxy-3-tert.-butylaminopropoxy)-6-methyl-2-benzimidazoline-thione hydrochloride; m.p. 294°–296° C.

EXAMPLE 6

4-(2-Hydroxy-3-tert.-butylaminopropoxy)-7-methyl-2-benzimidazoline-thione

Analogously to the process described in Example 3, from 2,3-diamino-1-(2-hydroxy-3-tert.-butylaminopropoxy)-4-methylbenzene, there is obtained 4-(2-hydroxy-3-tert.-butylaminopropoxy)-7-methyl-2-benzimidazoline-thione hydrochloride which, after recrystallisation from ethanol, decomposes at 298°–299° C.

The intermediate used in the above reaction can be prepared in the following manner:

2,3-Dinitro-4-methylphenol (see H. E. Dadswell and J. Kenner, J. Chem. Soc., 1927, 583) is reacted with 3-chloro-1,2-epoxypropane and 25% aqueous sodium hydroxide solution. There is obtained, in 78% yield, 2,3-dinitro-1-(2,3-epoxypropoxy)-4-methylbenzene; m.p. 121°–123° C. This compound is reacted in boiling ethanol with tert.-butylamine to give 2,3-dinitro-1-(2-hydroxy-3-tert.-butylaminopropoxy)-4-methylbenzene; m.p. 104°–106° C. By catalytic hydrogenation over platinum dioxide, there is obtained therefrom amorphous 2,3-diamino-1-(2-hydroxy-3-tert.-butylaminopropoxy)-4-methylbenzene in the form of its trihydrochloride.

EXAMPLE 7

6-tert.-Butyl-4-(2-hydroxy-3-tert.-butylaminopropoxy)-2-benzimidazoline-thione

From 5-tert.-butyl-2,3-diamino-1-(2-hydroxy-5-tert.-butylaminopropoxy)-benzene there is obtained, analogously to the process described in Example 3, 6-tert.-butyl-4-(2-hydroxy-3-tert.-butylaminopropoxy)-2-benzimidazoline-thione hydrochloride which decomposes above 280° C.

The diamino compound uses as intermediate can be synthesised via the following steps:

By the reaction of 4-tert.-butyl-2-(2,3-epxoypropoxy)-6-nitroaniline with tert.-butylamine, there is obtained 4-tert.-butyl-2-(2-hydroxy-3-tert.-butylaminopropoxy)-6-nitroaniline which is isolated as the hydrochloride with a decomposition point of 115°–120° C. Hydrogenation of this compound in ethanolic solution over platinum dioxide gives 5-tert.-butyl-2,3-diamino-1-(2-hydroxy-3-tert.-butylaminopropoxy)-benzene which is isolated as its amorphous trihydrochloride.

EXAMPLE 8

6,7-Dimethyl-4-(2-hydroxy-3tert.-butylaminopropoxy)-2-benzimidazoline-thione

Analogously to the process described in Example 3, from 2,3-diamino-4,5-dimethyl-1-(2-hydroxy-3-tert.-butylaminopropoxy)-benzene and potassium xanthogenate, there is obtained 6,7-dimethyl-4-(2-hydroxy-3-tert.-butylaminopropoxy)-2-benzimidazoline-thione hydrochloride which has a decomposition point of 307°–308° C.

The diamino compound required as intermediate is synthesised in the following manner from 2-amino-4,5-dimethylphenol (see E. Diepolder, Chem. Ber., 42, 2916/1909). This phenol compound is acetylated with acetic anhydride in ethyl acetate/pyridine to give 2-acetamido-1-acetoxy-4,5-dimethylbenzene (m.p. 156°–158° C.) which is nitrated in acetic anhydride with 100% nitric acid in acetic anhydride at 20° C. From the nitration mixture there is isolated, in 43% yield, 2-acetamido-1-acetoxy-4,5-dimethyl-3-nitrobenzene; m.p. 209°–211° C. After saponification of this compound in 2 N hydrochloric acid, there is isolated 2-amino-4,5-dimethyl-3-nitrophenol; m.p. 176°–178° C. This compound is converted into the sodium salt with a methanolic solution of sodium methylate. This salt is reacted in dioxan/dimethylformamide with excess 3-chloro-1,2-epoxypropane at 75° C. After evaporation, the residue is taken up in chloroform, treated with water and active charcoal and freed from solvent. The amorphous residue of 2-amino-4,5-dimethyl-1-(2,3-epoxypropoxy)-3-nitrobenzene is reacted in boiling ethanol with tert.-butylamine to give 2-amino-4,5-dimethyl-1-(2-hydroxy-3-tert.-butylaminopropoxy)-3-nitrobenzene. This compound is then quantitatively hydrogenated in ethanol over platinum dioxide to give 2,3-diamino-4,5-dimethyl-1-(2-hydroxy-3-tert.-butylaminopropoxy)-benzene, which is isolated as its trihydrochloride.

The following tests were carried out to determine the cardiac β-receptor blocking activity of certain test compounds by determining the inhibition of the heart beat frequency increase induced by intravenous administration of isoprenalin (=3,4-dihydroxy-α-[(isopropylamino)-methyl]-benzylalcohol).

The test compounds representative of the invention were the following (prepared as set forth in Examples 1–8, supra, respectively):

| | |
|---|---|
| Compound I | 4-(2-Hydroxy-3-tert.-butylamino-propoxy)-2-benzimidazoline-thione |
| Compound II | 4-[2-Hydroxy-3-(2-propylamino)-propoxy]-2-benzimidazoline-thione |
| Compound III | 4-(2-Hydroxy-3-tert.-butylamino-propoxy)-6-methyl-2-benzimidazoline-thione |
| Compound IV | 4-[2-Hydroxy-3-(2-propylamino)-propoxy]-6-methyl-2-benzimidazoline-thione |
| Compound V | 4-(2-Pivaloyloxy-3-tert.-butylamino-propoxy)-6-methyl-2-benzimidazoline-thione |
| Compound VI | 4-(2-Hydroxy-3-tert.-butylamino-propoxy)-7-methyl-2-benzimidazoline-thione |
| Compound VII | 6-tert.-Butyl-4-(2-hydroxy-3-tert.-butylamino-propoxy)-2-benzimidazoline-thione |
| Compound VIII | 6,7-Dimethyl-4-(2-hydroxy-3-tert.-butylamino-propoxy-2-benzimidazoline-thione |

As comparison compound there was included:

| | |
|---|---|
| Compound A | 1-Isopropylamino-3-(1-naphthoxy)-2-propanol (Propranolol) |

Table 1

| | Blocking of Isoprenalin Tachycardia In Wake Rabbits (1 μg/kg i.v.) | | |
|---|---|---|---|
| | Dosage mg/kg i.v. | Heartbeat Frequency (min) $\bar{x} \pm S\bar{x}$ | DE 250* μg/kg i.v. |
| Control | without Isoprenalin | 209 ± 9 | — |
| Control | with Isoprenalin | 338 ± 10 | — |
| Compound A (Propranolol) | 0.05 | 316 ± 5 | |
| | 0.1 | 285 ± 6 | |
| | 0.2 | 269 ± 7 | 422 ± 110 |
| | 0.4 | 245 ± 3 | |
| | 0.8 | 235 ± 4 | |
| | 1.6 | 222 ± 5 | |
| Compound I | 0.00025 | 326 ± 6 | |
| | 0.0005 | 316 ± 9 | |
| | 0.001 | 276 ± 7 | 1.9 ± 0.3 |
| | 0.002 | 238 ± 7 | |
| | 0.004 | 235 ± 4 | |
| | 0.008 | 230 ± 7 | |
| Compound II | 0.001 | 309 ± 7 | |
| | 0.002 | 269 ± 6 | |
| | 0.004 | 247 ± 12 | 4.56 ± 1.09 |
| | 0.008 | 229 ± 8 | |
| | 0.016 | 226 ± 7 | |
| | 0.032 | 218 ± 6 | |
| Compound III | 0.0005 | 297 ± 9 | |
| | 0.001 | 263 ± 12 | |
| | 0.002 | 218 ± 10 | 1.3 ± 0.21 |
| | 0.004 | 212 ± 9 | |
| | 0.008 | 208 ± 7 | |
| | 0.016 | 200 ± 6 | |
| Compound IV | 0.001 | 287 ± 5 | |
| | 0.002 | 238 ± 8 | |
| | 0.004 | 203 ± 7 | |
| | 0.008 | 187 ± 5 | 1.87 ± 0.12 |
| | 0.016 | 186 ± 4 | |
| | 0.032 | 189 ± 6 | |
| Compound V | 0.001 | 311 ± 12 | |
| | 0.002 | 303 ± 6 | |
| | 0.004 | 268 ± 11 | 6.31 ± 1.13 |

Table 1-continued

| | Blocking of Isoprenalin Tachycardia In Wake Rabbits (1 μg/kg i.v.) | | |
|---|---|---|---|
| | Dosage mg/kg i.v. | Heartbeat Frequency (min) x̄ ± S x̄ | DE 250* μg/kg i.v. |
| | 0.008 | 229 ± 11 | |
| | 0.016 | 215 ± 12 | |
| | 0.032 | 205 ± 10 | |
| Compound VI | 0.0005 | 312 ± 13 | |
| | 0.0010 | 260 ± 18 | |
| | 0.002 | 237 ± 14 | 1.7 ± 0.49 |
| | 0.004 | 202 ± 14 | |
| | 0.008 | 193 ± 10 | |
| | 0.016 | 190 ± 12 | |
| Compound VII | 0.002 | 313 ± 12 | |
| | 0.004 | 315 ± 12 | |
| | 0.008 | 282 ± 12 | 21.08 ± 1.71 |
| | 0.016 | 278 ± 13 | |
| | 0.032 | 210 ± 8 | |
| | 0.064 | 194 ± 9 | |
| Compound VIII | 0.0005 | 311 ± 4 | |
| | 0.001 | 284 ± 2 | |
| | 0.002 | 245 ± 7 | |
| | 0.008 | 201 ± 4 | 1.95 ± 0.16 |
| | 0.016 | 197 ± 5 | |

*Interpolated dosage which limits the frequency increase to 250 beats/min.

These compounds were tested as follows:

The β-receptor blocking activity of the test compounds was tested on wake rabbits weighing between 2 to 3.5 kg and kept in wooden cages. EKG-electrodes were inserted into the hind quarters of the rabbits subcutaneously and the heart frequency was determined using a frequency counter (15 seconds) as a digital value. The test compounds were then injected through a small tube to the ear vein of the rabbits at 10 minute intervals in logarithmically increasing dosages and, 10 minutes after each infusion, isoprenalin was injected intravenously at 1 μg/kg.

The results are set forth in the above table.

The above data show that the inventive compounds are already effective at a dosage much smaller than those required of the comparison substance.

The compounds according to the present invention are thus unexpectedly superior in effectiveness to known compounds and thus present a valuable contribution to the art.

The dosages of the novel compounds of the present invention depend on the age, weight, and condition of the patient being treated. Generally speaking, for adultoral administration, the preferred unit dosage of active compound with suitable pharmaceutical diluent or lubricant is 1 mg.–40 mg., four times a day. In general the oral dosage is 20–40 mg., whereas the intravenous dosage is generally 1–5 mg., four times a day.

For preparing therapeutic compositions, such as tablets and other compressed formulations, the compounds can include any compatible and edible tableting material used in pharmaceutical practice, as for example, corn starch, lactose, stearic acid, magnesium stearate, talc, methyl cellulose, and the like.

Similarly, the compounds of the present invention can be mixed with suitable adjuvants for the preparation of resorbable hard gelatin or soft capsules utilizing conventional pharmaceutical practices.

Further, the compounds can be employed in the form of their solutions or suspensions suitable for parenteral administrations.

It will be understood that the specification and examples are illustrative but not limitative of the present invention and that other embodiments within the spirit and scope of the invention will suggest themselves to those skilled in the art.

What is claimed is:

1. 4-Hydroxy-2-benzimidazoline-thione compound of the formula

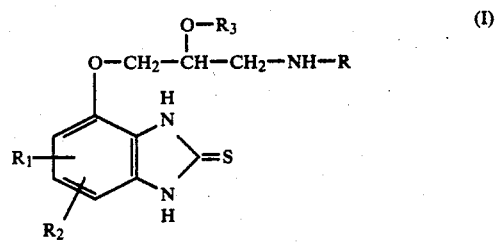

wherein

R is lower alkyl of up to 6 carbon atoms;

$R_1$ and $R_2$, which can be the same or different, are hydrogen or lower straight-chained or branched alkyl of up to 6 carbon atoms or $R_1$ and $R_2$ together represent alkylene of 2 to 4 carbon atoms; and $R_3$ is alkanoyl of up to 6 carbon atoms, or aroyl up to 7 carbon atoms;

and the pharmacologically acceptable salts thereof.

2. 4-Hydroxy-2-benzimidazoline-thione compound as claimed in claim 1 wherein $R_1$ and $R_2$ are both hydrogen.

3. 4-Hydroxy-2-benzimidazoline-thione compound as claimed in claim 1 wherein $R_1$ and $R_2$ are both alkyl of up to 6 carbon atoms.

4. 4-Hydroxy-2-benzimidazoline-thione compound as claimed in claim 1 wherein one of $R_1$ and $R_2$ is hydrogen and the other is alkyl of up to 6 carbon atoms.

5. 4-Hydroxy-2-benzimidazoline-thione compond as claimed in claim 1 wherein $R_1$ and $R_2$ together are alkylene of 2 to 4 carbon atoms.

6. 4-Hydroxy-2-benzimidazoline-thione compound as claimed in claim 1 wherein $R_3$ is hydrogen.

7. 4-Hydroxy-2-benzimidazoline-thione compound as claimed in claim 1 wherein $R_3$ is alkanoyl of up to 6 carbon atoms.

8. 4-Hydroxy-2-benzimidazoline-thione compound as claimed in claim 1 wherein $R_3$ is the acid residue of an aromatic carboxylic acid, containing up to 7 carbon atoms.

9. 4-Hydroxy-2-benzimidazoline-thione compound as claimed in claim 1 designated 4-(2-hydroxy-3-tert.-butylaminopropoxy)-2-benzimidazoline-thione.

10. 4-Hydroxy-2-benzimidazoline-thione compound as claimed in claim 1 designated 4-(2-hydroxy-3-tert-butylaminopropoxy)-6-methyl-2-benzimidazoline-thione.

11. 4-Hydroxy-2-benzimidazoline-thione compound as claimed in claim 1 designated 4-[2-hydroxy-3-(2-propylamino)-propoxy]-6-methyl-2-benzimidazoline-thione.

12. 4-Hydroxy-2-benzimidazoline-thione compound as claimed in claim 1 designated 4-(2-hydroxy-3-tert.-butylaminopropoxy)-7-methyl-2-benzimidazoline-thione.

13. 4-Hydroxy-2-benzimidazoline-thione compound as claimed in claim 1 designated 6,7-dimethyl-4-(2-hydroxy-3-tert.-butylamino-propoxy)-2-benzimidazoline-thione.

14. Therapeutic compositions for the treatment of cardiac and circulatory infirmities which composition comprises a pharmacologically acceptable carrier and, in effective amounts, a 4-hydroxy-2-benzimidazoline-thione compound as claimed in claim 1.

15. Therapeutic composition as claimed in claim 14 wherein said 4-hydroxy-2-benzimidazoline-thione compound is one of
4-(2-hydroxy-3-tert.-butylamino-propoxy)-2-benzimidazoline-thione
4-(2-hydroxy-3-tert.-butylamino-propoxy)-6-methyl-2-benzimidazoline-thione
4-[2-hydroxy-3-(2-propylamino)-propoxy]-6-methyl-2-benzimidazoline-thione
4-(2-hydroxy-3-tert.-butylamino-propoxy)-7-methyl-2-benzimidazoline-thione and
6,7-dimethyl-4-(2-hydroxy-3-tert.-butylaminopropoxy)-2-benzimidazoline-thione.

16. Method of treating circulatory and cardiac diseases which method comprises applying to an afflicted subject a therapeutically effective amount of a 4-hydroxy-2-benzimidazoline-thione compound as claimed in claim 1.

17. Method as claimed in claim 16 wherein said compound is at least one of the following:
4-(2-hydroxy-3-tert.-butylamino-propoxy)-2-benzimidazoline-thione
4-(2-hydroxy-3-tert.-butylamino-propoxy)-6-methyl-2-benzimidazoline-thione
4-[2-hydroxy-3-(2-propylamino)-propoxy]-6-methyl-2-benzimidazoline-thione
4-(2-hydroxy-3-tert.-butylamino-propoxy)-7-methyl-2-benzimidazoline-thione and
6,7-dimethyl-4-(2-hydroxy-3-tert.-butylaminopropoxy)-2-benzimidazoline-thione.

18. Method as claimed in claim 16 wherein said compound is applied at a dosage of 1 mg–40 mg four times a day adultorally.

19. Method as claimed in claim 16 wherein said compound is applied at a dosage of 20 mg–40 mg four times a day applied orally.

20. Method as claimed in claim 16 wherein said compound is applied at a dosage of 1 mg–5 mg four times a day applied intravenously.

* * * * *